US012551615B2

(12) United States Patent
Cole et al.

(10) Patent No.: US 12,551,615 B2
(45) Date of Patent: Feb. 17, 2026

(54) CATHETER INSERTION DEVICE

(71) Applicant: Becton, Dickinson and Company, Franklin Lakes, NJ (US)

(72) Inventors: Russell Cole, River Vale, NJ (US); Michael Creighton, Hatboro, NJ (US); Gary Reuther, Warminster, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1137 days.

(21) Appl. No.: 17/521,059

(22) Filed: Nov. 8, 2021

(65) Prior Publication Data

US 2022/0054744 A1 Feb. 24, 2022

Related U.S. Application Data

(63) Continuation of application No. 16/276,373, filed on Feb. 14, 2019, now Pat. No. 11,191,894, which is a (Continued)

(51) Int. Cl.
*A61M 5/158* (2006.01)
*A61M 25/06* (2006.01)

(52) U.S. Cl.
CPC ........ *A61M 5/158* (2013.01); *A61M 25/0606* (2013.01); *A61M 2005/1585* (2013.01)

(58) Field of Classification Search
CPC .................. A61M 5/158; A61M 5/142; A61M 2005/14252; A61M 2005/1588;

(Continued)

(56) References Cited

U.S. PATENT DOCUMENTS

| | | | | |
|---|---|---|---|---|
| 5,385,551 A | 1/1995 | Shaw | | |
| 11,786,653 B2 * | 10/2023 | Gyrn | A61M 5/158 604/157 | |

(Continued)

FOREIGN PATENT DOCUMENTS

| | | |
|---|---|---|
| WO | WO-2009158651 A2 | 12/2009 |
| WO | WO-2011121023 A1 | 10/2011 |
| WO | WO-201386439 A1 | 6/2013 |

OTHER PUBLICATIONS

English translation of the Japanese Office Action dated Jun. 4, 2019, which issued in the corresponding Japanese Patent Application No. 2016-563972.

(Continued)

*Primary Examiner* — Kevin C Sirmons
*Assistant Examiner* — Antarius S Daniel
(74) *Attorney, Agent, or Firm* — Dickinson Wright PLLC

(57) ABSTRACT

A catheter insertion device (10) includes a housing (12) with a base (14), a catheter (28), an introducer needle (30) and an actuator (26) mounted within the housing. The catheter (28) and needle (30) are coupled to the actuator (26) and movable between a first position where the catheter and needle are retracted within the housing and a second position where the catheter (28) and needle (30) extend from the housing, and where the needle retracts into the actuator when the catheter and needle reach the second position. A spring (90) is provided in the housing (12) or the actuator (26) where the spring (90) is released after deployment of the device to retract the needle (20) with respect to the catheter (28).

20 Claims, 16 Drawing Sheets

Related U.S. Application Data continuation of application No. 15/301,186, filed as application No. PCT/US2015/027369 on Apr. 23, 2015, now Pat. No. 10,251,999.

(60) Provisional application No. 61/983,982, filed on Apr. 24, 2014.

(58) Field of Classification Search
CPC ...... A61M 2205/0216; A61M 2205/18; A61M 2205/33; A61M 2205/50; A61M 2005/14256; A61M 2039/0267; A61M 25/0606; A61M 2005/1585
See application file for complete search history.

(56) References Cited

U.S. PATENT DOCUMENTS

| | | | | |
|---|---|---|---|---|
| 2007/0093754 | A1* | 4/2007 | Mogensen | A61M 25/0612 604/164.12 |
| 2008/0051714 | A1 | 2/2008 | Moberg et al. | |
| 2009/0099521 | A1 | 4/2009 | Gravesen et al. | |
| 2009/0326454 | A1 | 12/2009 | Cross et al. | |
| 2011/0257597 | A1 | 10/2011 | Safabash et al. | |
| 2013/0079719 | A1 | 3/2013 | Gyrn | |
| 2013/0237918 | A1 | 9/2013 | Gyrn | |
| 2014/0088509 | A1 | 3/2014 | Sonderegger et al. | |

OTHER PUBLICATIONS

International Search Report and Written Opinion dated Jul. 28, 2015 issued in the corresponding PCT Patent Application No. PCT/US2015/027369.

Chinese Office Action dated Feb. 10, 2017 which issued in the corresponding Patent Application No. 201590000457.0, including English translation.

* cited by examiner

CATHETER INSERTION DEVICE

CROSS-REFERENCE TO RELATED APPLICATION

This application is a continuation of U.S. Ser. No. 16/276,373, filed on Feb. 14, 2019, which is a continuation application of U.S. Ser. No. 15/301,186, filed on Sep. 30, 2016, which is a 371 application of PCT/US2016/027369, which claims priority under 35 USC § 119(e) from U.S. Provisional Patent Application Ser. No. 61/983,982 filed on Apr. 24, 2014, the disclosure of which is incorporated herein by reference in its entirety.

FIELD OF THE INVENTION

The present invention is directed to a catheter insertion device and to an infusion set including the catheter insertion device. The invention is particularly directed to a catheter insertion device for use with an infusion set or other delivery device for introducing a catheter into a patient and automatically retracting an insertion needle once the catheter is moved to an extended position with respect to a housing of the device. The invention is also directed to a manually operated catheter insertion device where an actuator is deployed to insert the catheter into the patient and automatically retract the insertion needle. The invention is further directed to a method of inserting a catheter using the catheter insertion device of the invention.

BACKGROUND OF THE INVENTION

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted onto the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set.

A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

In order to minimize the height of the insertion mechanism, some conventional insertion mechanisms are configured to insert the cannula at an acute angle from the surface of the skin, e.g. 30-45 degrees. However, it may be preferable to insert the cannula perpendicular or close to the perpendicular from the surface of the skin, since this would require the minimum length of cannula insertion. In other words, with the minimum length of cannula being inserted into the user's skin, the user can experience greater comfort and fewer complications, such as premature kinking of the cannula. But one problem with configuring the insertion mechanism to insert the cannula perpendicular to the surface of the skin is that this may increase the overall height of the insertion mechanism, and therefore of the patch pump itself.

Accordingly, a need exists for an improved insertion mechanism for use in a limited space environment, such as in the patch pump, that can cost-effectively insert a cannula vertically or close to perpendicularly into the surface of a user's skin, while minimizing or reducing its height, in order to reduce the overall height of the device the insertion mechanism is incorporated into, such as a patch pump.

SUMMARY OF THE INVENTION

The present invention is directed to a catheter insertion device for use with an infusion set or patch pump. The invention is particularly directed to a catheter insertion device having an actuator that is manually depressed to insert the catheter by the use of an insertion needle into the patient and to automatically retract the insertion needle from the catheter when the catheter is deployed to a predetermined depth.

One embodiment of the invention is to provide an infusion set having a self-contained catheter insertion or introducing device that deploys the catheter and retracts the insertion needle in a single operation by the user.

Another feature of the invention is to provide a catheter insertion device having a manually operated actuator that is pressed by the user to insert the catheter into the patient and where the actuator automatically releases the introducer needle when the catheter is moved to an extended position to retract the introducer needle into the housing of the device.

Another feature of the invention is to provide a catheter insertion device where a catheter and an insertion needle are movable between a first retracted position and a second extended position. A catheter hub receives an insertion needle during movement to the second position where the needle then retracts at least partially from the catheter hub. A spring can be provided to automatically retract the needle with respect to the catheter and catheter hub when the catheter and insertion needle are deployed.

In one embodiment of the invention, the spring is initially in a compressed condition and is released by movement of the actuator after deployment of the catheter. The spring can be mounted to the base of the housing or to the actuator. In one embodiment, the spring and a spring retainer are coupled to the housing and configured so that the when the catheter and needle are deployed, the catheter hub contacts the spring retainer and separates from the spring to deploy the spring which then retracts the needle into the actuator.

In another embodiment, the spring and spring retainer are coupled to the actuator. The spring is retained in the compressed condition by the spring retainer during movement of the actuator to an extended position where the catheter and insertion needle penetrate the skin of the patient. The spring retainer contacts the base of the housing when the catheter and needle are completely extended to release and disengage the spring retainer from the spring. The spring is then allowed to expand and carry the needle away from the base and retract the needle from the catheter.

These and other aspects of the invention are basically attained by providing a catheter insertion device having a housing with a base, a catheter movable between a first retracted position and a second extended position with respect to the housing, an introducer needle within the catheter and movable between a first retracted position and a second extended position with respect to the base, and an actuator for actuating the device. A spring and spring retainer are disposed in the housing to retain the spring in an initial compressed condition. The catheter and needle are coupled to the actuator and are movable between a first position where the catheter and needle are retracted within the housing and a second position where the catheter and needle extend from the housing, and where the retainer releases the spring when the actuator is moved to the second position to automatically retract the needle into the actuator.

The various aspects of the invention are also attained by providing a catheter insertion device comprising a housing with a base, a catheter, an introducer needle and an actuator. The catheter is coupled to the actuator and is movable between a first retracted position and a second extended position with respect to the housing. The introducer needle is positioned within the catheter and is movable between a first retracted position and a second extended position with respect to the base. A spring and a spring retainer are disposed in the housing to retain the spring in an initial compressed condition. The needle is slidably received within the actuator where the actuator is movable between a first position where the catheter and needle are in the respective first positions within the housing, and a second position where the catheter and needle are in the respective second positions and the catheter hub engages the spring retainer to release the spring. The needle carrier is releasably coupled to a distal end of the catheter. The needle carrier is separated from the catheter when the spring is released to retract the needle into the actuator.

The features of the invention are also provided by a catheter insertion device comprising a housing having a base, and an actuator coupled to the base. A catheter hub is coupled to the actuator and a catheter coupled to the catheter hub where the actuator and catheter hub are being movable between a first position disposed where the catheter is within the base and a second position where the catheter extends from the base when the actuator is in the second position. An introducer needle is slidably received in the actuator and slidable between a first extended position with respect to the actuator and catheter holder, and a second retracted position where the needle carrier is releasably coupled to the catheter hub. A spring and spring retainer for retaining the spring in a compressed condition are positioned in the housing. The catheter hub is configured to release the spring to automatically retract the needle when the catheter and catheter hub are moved to the second position.

These and other aspects of the invention will become apparent from the following detailed description of the invention which, taken in conjunction with the annexed drawings, show various embodiments of the invention.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE INVENTION

Figure 1:
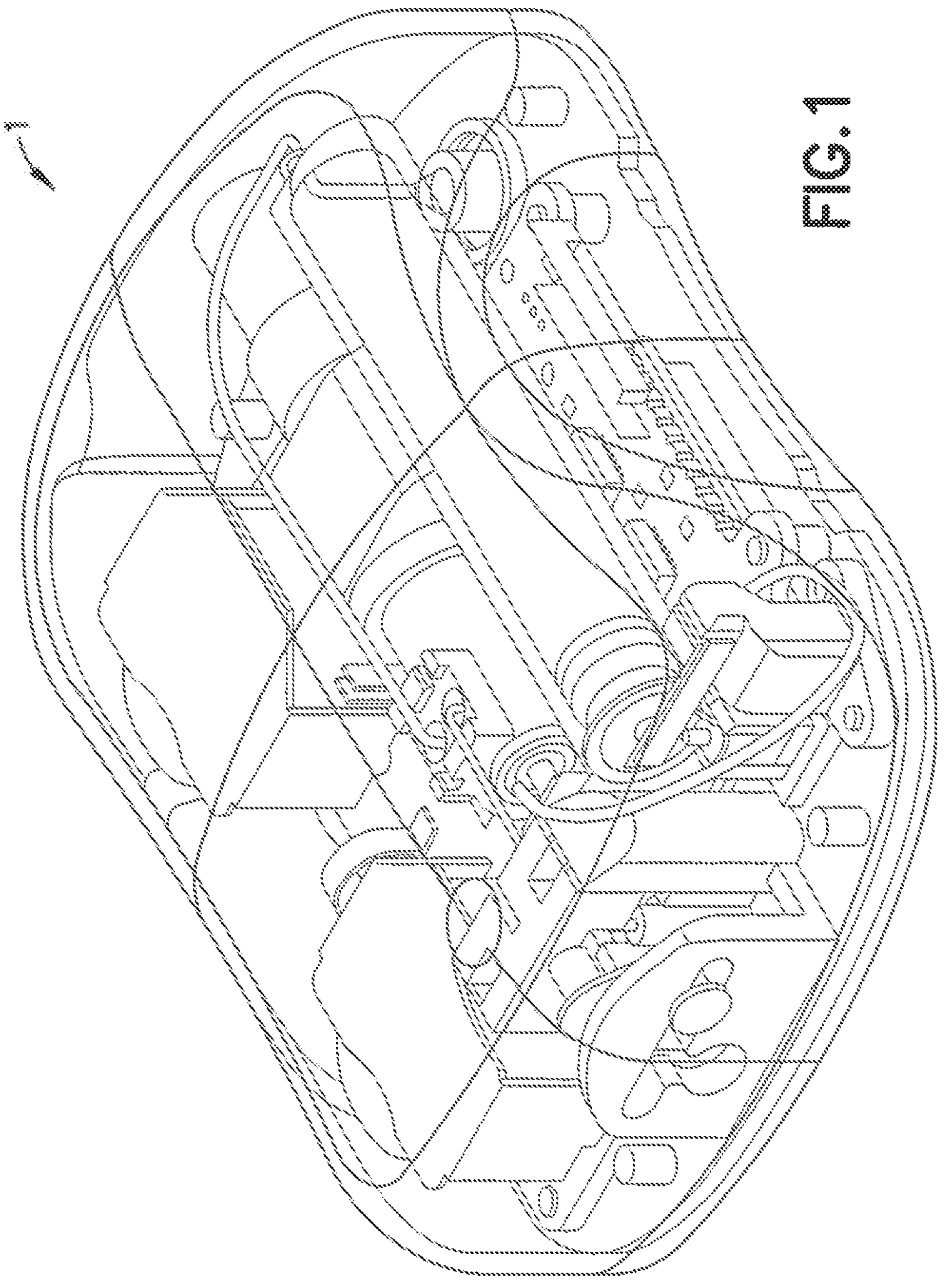
FIG. 1 is a perspective view of a patch pump incorporating a low-profile cannula insertion device, illustrated with a transparent cover for clarity.
Figure 2:
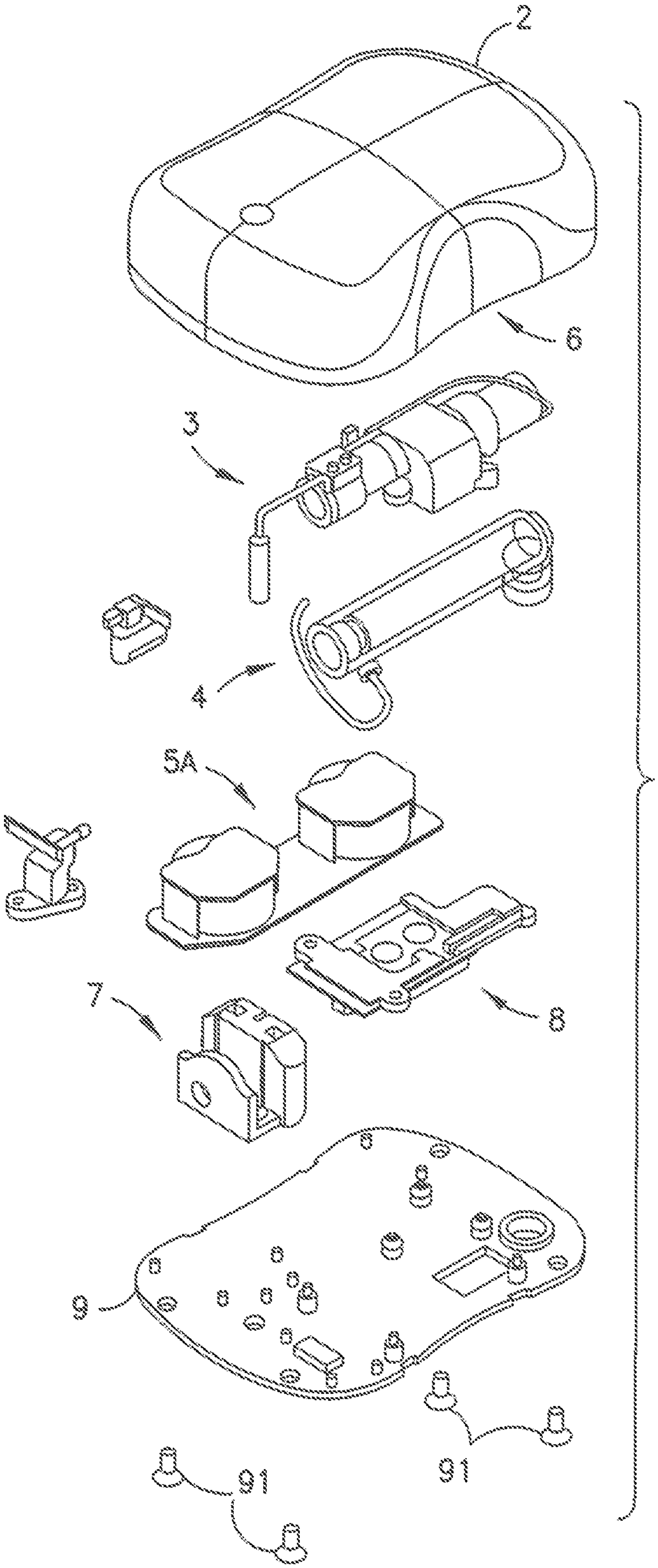
FIG. 2 is an exploded view of the various components of the patch pump of FIG. 1, illustrated with a cover.

FIG. 1 is a perspective view of an exemplary embodiment of a patch pump 1 according to an exemplary embodiment of the invention. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include: a reservoir 4 for storing insulin; a pump 3 for pumping insulin out of the reservoir 4; a power source 5 in the form of one or more batteries; an insertion mechanism 7 for inserting an inserter needle with a catheter into a user's skin; control electronics 8 in the form of a circuit board with optional communications capabilities to outside devices such as a remote controller and computer, including a smart phone; a dose button 6 on the cover 2 for actuating an insulin dose, including a bolus dose; and a base 9 to which various components above may be attached via fasteners 91. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to reliably penetrate the skin, but otherwise may be made flexible enough to provide comfort to the user.

Figure 3:
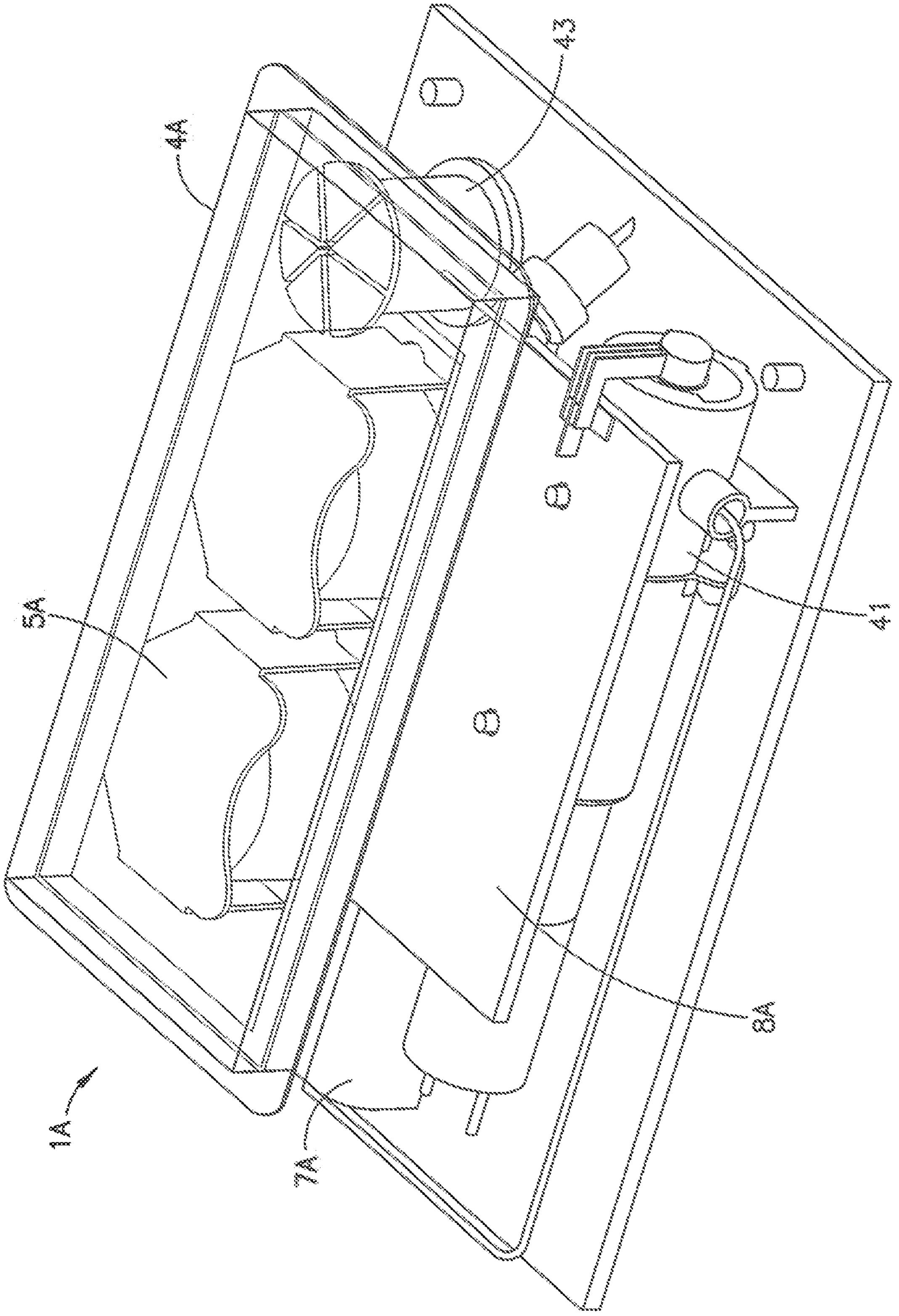
FIG. 3 is a perspective view of an alternative design for a patch pump having a flexible reservoir, illustrated without a cover.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
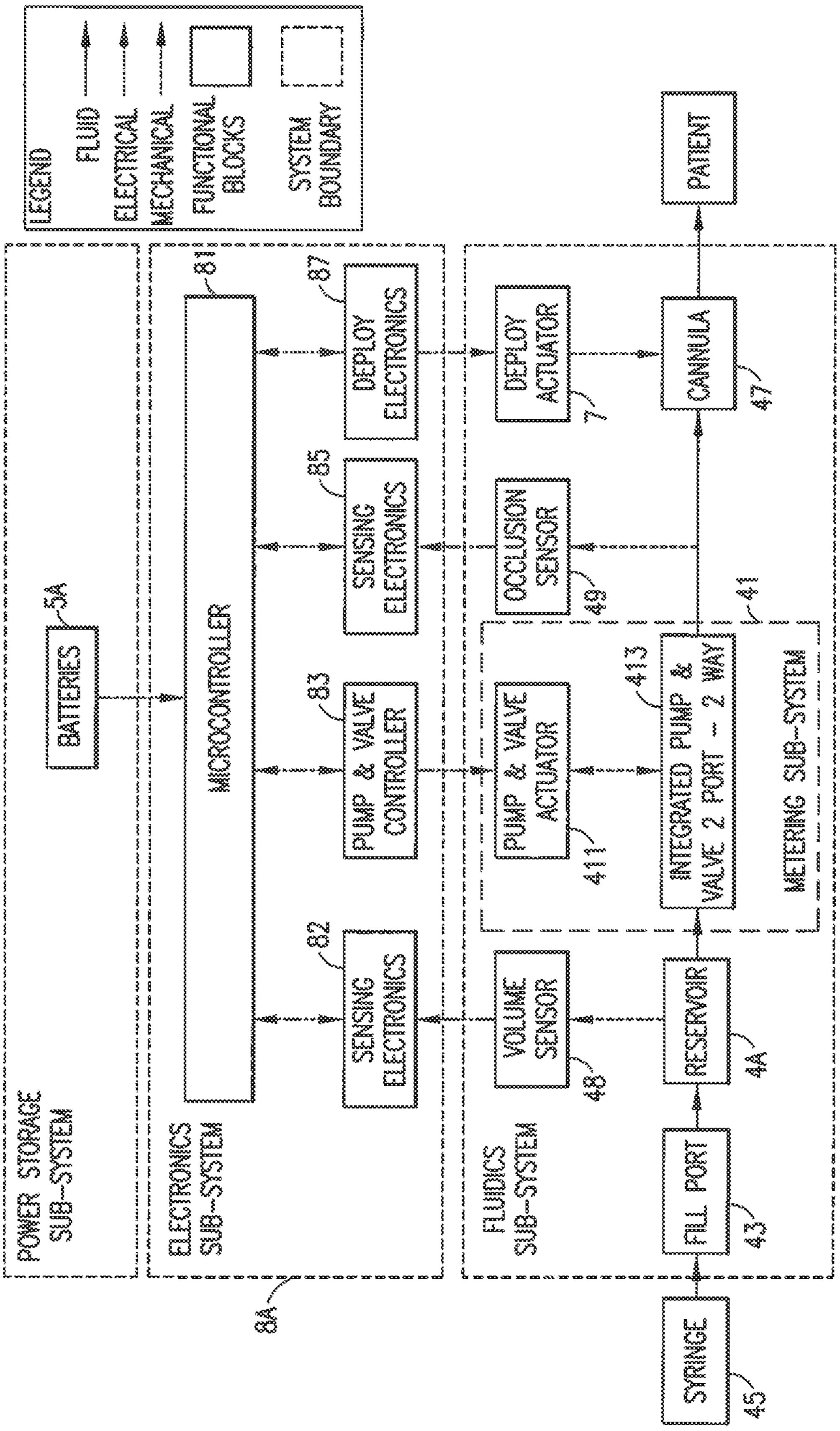
FIG. 4 is a patch-pump fluidic architecture and metering sub-system diagram of the patch pump of FIG. 3.
Figure 5:
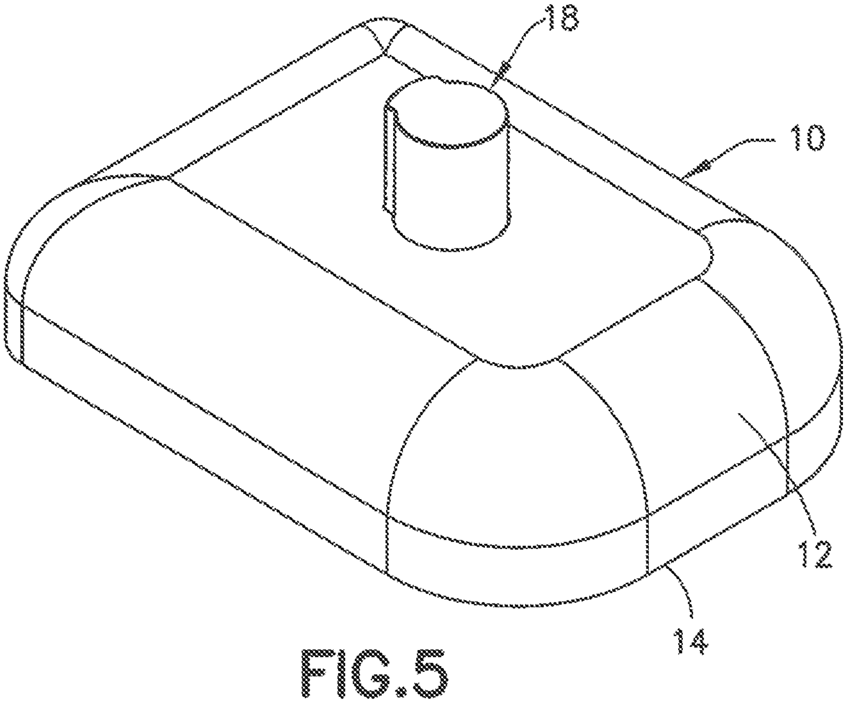
FIG. 5 is a perspective view of a patch pump or infusion set including the catheter insertion device in one embodiment of the invention.
Figure 6:
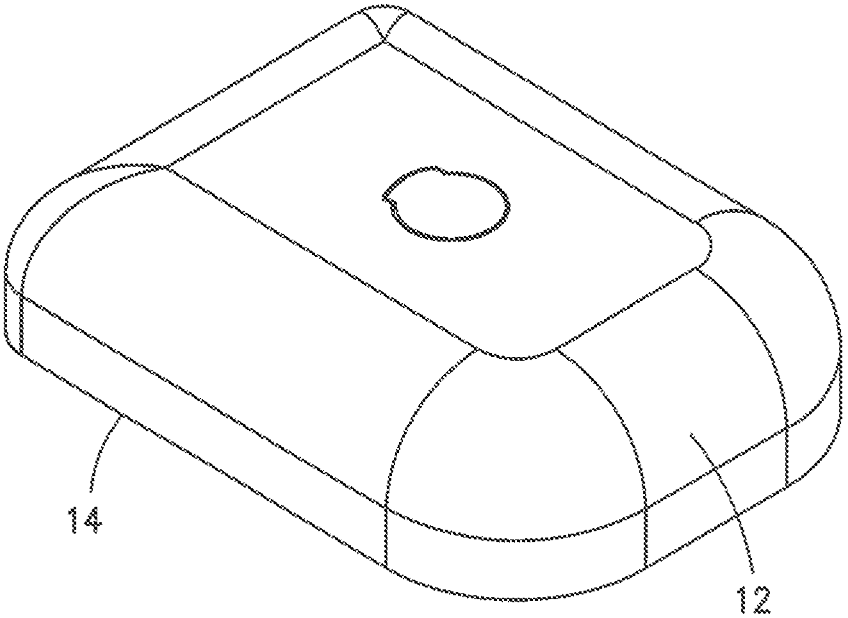
FIG. 6 is a perspective view of the patch pump showing the actuator in the deployed position.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 47 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

The present invention is directed to a catheter insertion device for use with the infusion set or patch pump. The invention is particularly directed to a catheter insertion device having an actuator that is manually depressed to insert the catheter into the patient and automatically release a spring to retract the insertion needle from the catheter into the actuator.

Referring to FIGS. 5-13, a patch pump, also referred to herein as an infusion set 10, is provided for introducing a drug or pharmaceutical to a patient need thereof. The infusion set of the invention can be for use with insulin injection systems, although other drugs or pharmaceuticals can be delivered to the patient. The infusion set contains a suitable dispensing mechanisms, storage containers and metering devices for extended delivery of the drug or pharmaceutical to the patient as known in the art. The invention is further directed to a method of inserting a catheter using the insertion device.

A housing 12 has a base 14 with an internal cavity for containing the fluid supply or reservoir and metering mechanisms for delivering insulin, drug, pharmaceutical or other medicament to the patient. A catheter insertion device 18 is mounted within the housing 12 and the base 14. In the embodiment shown, the base 14 is constructed to contact the skin of the patient for delivering the medicament to the patient.

The catheter insertion device 18 includes an actuator 26, a delivery device shown as a catheter 28, and an insertion needle 30. In the embodiment of the invention as shown, the delivery device is a flexible catheter 28 as known in the art having a dimension and length suitable for delivering insulin or other drugs and pharmaceuticals through the skin of a patient with minimal discomfort to the patient. Flexible catheters are generally preferred to reduce the discomfort to the patient. In other embodiments, the delivery device can be a rigid cannula or lumen.

Figure 8:
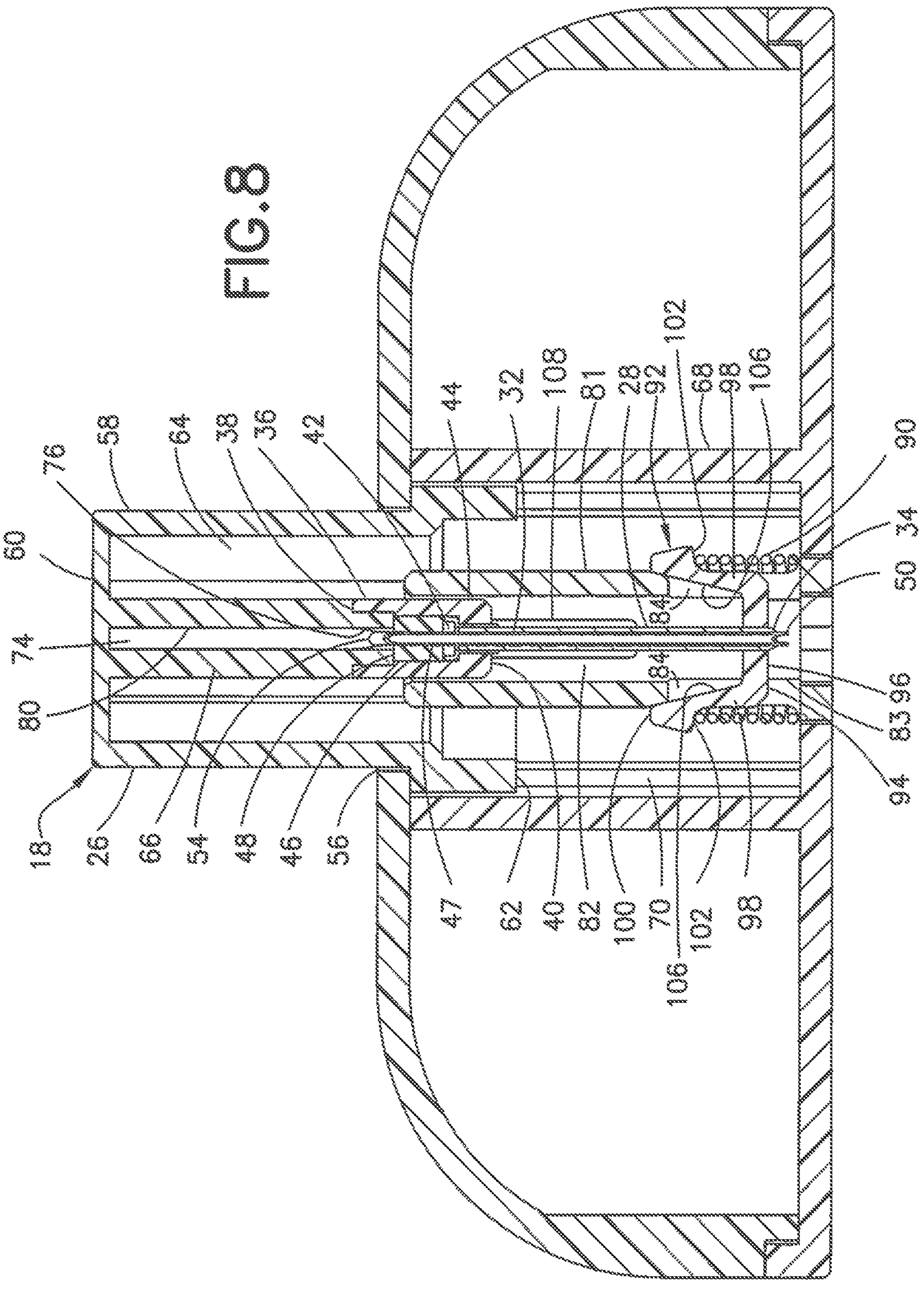
FIG. 8 is a partial cross-sectional view showing the insertion device in the initial position with the spring in the compressed state.

Catheter 28 has a first proximal end 32 and a second distal outer end 34. A fluid passage extends between the ends for delivering the insulin or other drug or pharmaceutical to the patient. First end 32 of catheter 28 is coupled to a catheter hub 36 as shown in FIG. 8. Catheter hub 36 has a substantially cylindrical shape in the embodiment shown for sliding movement within housing 12. Catheter hub 36 has a passage extending between a first end 38 and a second end 40 having a cavity for receiving a generally funnel shaped member 42. Funnel shaped member 42 has a neck 44 inserted into the passage of catheter 28 at the first proximal end 32 by a friction fit or adhesive to couple catheter 28 to catheter hub 36. Funnel shaped member 42 has an upper end 46 with a septum 48.

Figure 10:
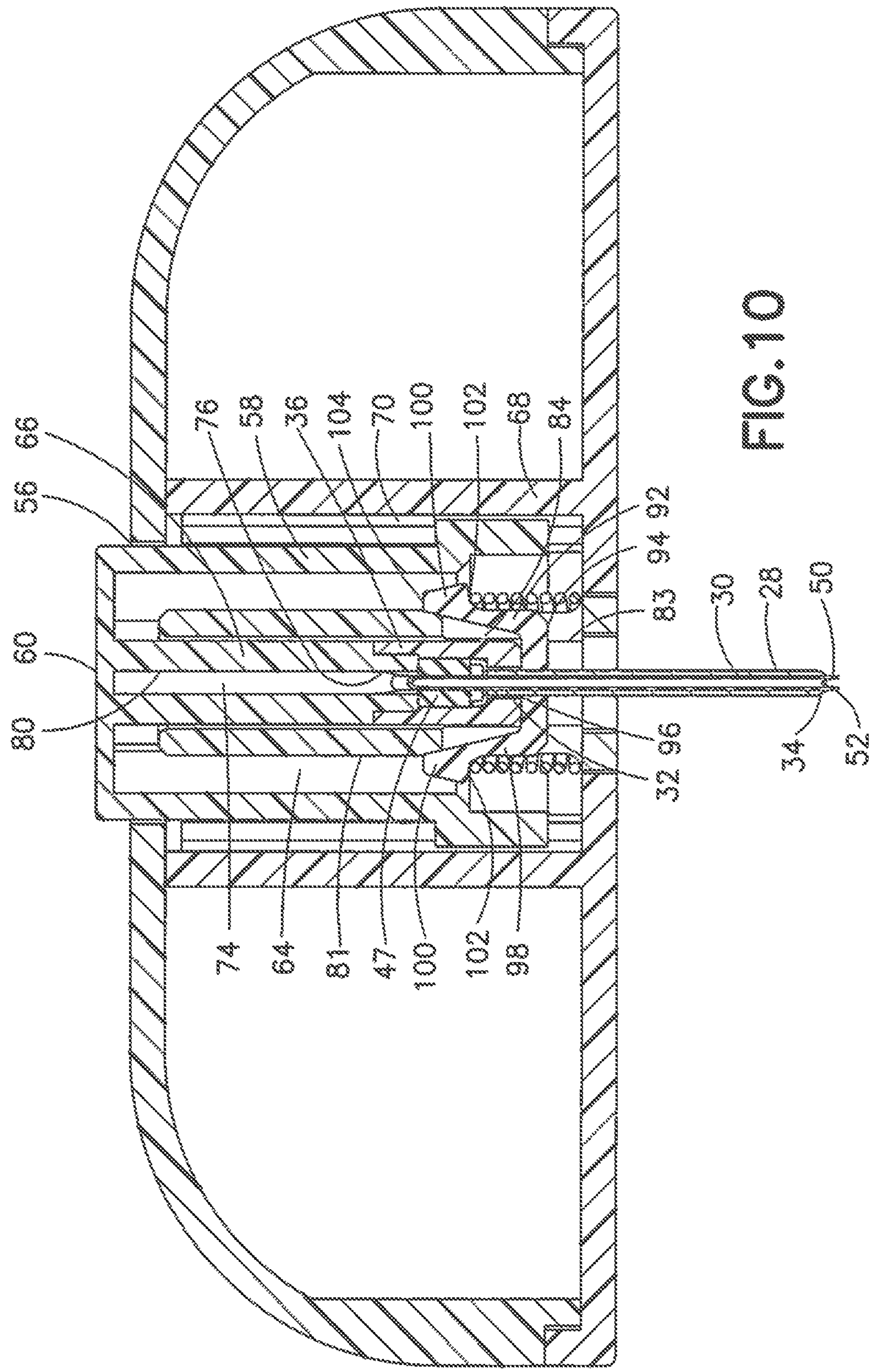
FIG. 10 is a cross-sectional view showing the catheter and needle in the extended, partially deployed position.

Insertion needle 30 is received in the passage of catheter 28 and has a length to extend past distal end 34 of catheter 28 as shown in FIG. 8. Insertion needle 30 in the embodiment shown is a steel cannula having an internal passage for delivering insulin or other pharmaceutical agents to catheter 28 and to the patient. Insertion needle 30 has a pointed distal end 50 with a sharp tip 52 for penetrating the skin of the patient to assist in inserting flexible catheter 28 into the skin of the patient as shown in FIG. 10. Insertion needle 30 passes through septum 48 to provide a fluid tight seal between insertion needle 30 and catheter 28 as known in the art. As shown in FIG. 8, insertion needle 30 has a connecting section 54 connected to the delivery device and fluid supply, such as the supply shown in FIG. 3, contained within the housing 12 for delivering the insulin or pharmaceutical agent to the patient. As shown in the drawings, insertion needle 30 is mounted for sliding movement within actuator 26 and housing 12 in a substantially linear direction. In one embodiment as shown, insertion needle 30 travels in a direction substantially perpendicular to the plane of the base 14. The connecting portion 54 is received in a slot or notch in catheter hub 36 by a friction fit so that needle 30 travels with catheter hub 36 and catheter 28 until separated.

Actuator 26 is in the form of a button or other manually actuated member that is depressed or actuated by the patient during use and deployment and insertion of the catheter 28 into the patient. Actuator 26 is movable from a first position shown in FIG. 8 to an actuated or deployed position shown in FIGS. 10 and 11. Actuator 26 in the embodiment shown has a substantially cylindrical configuration and is received within an opening 56 in a top face of housing 12 for sliding movement within opening 56.

Figure 7:
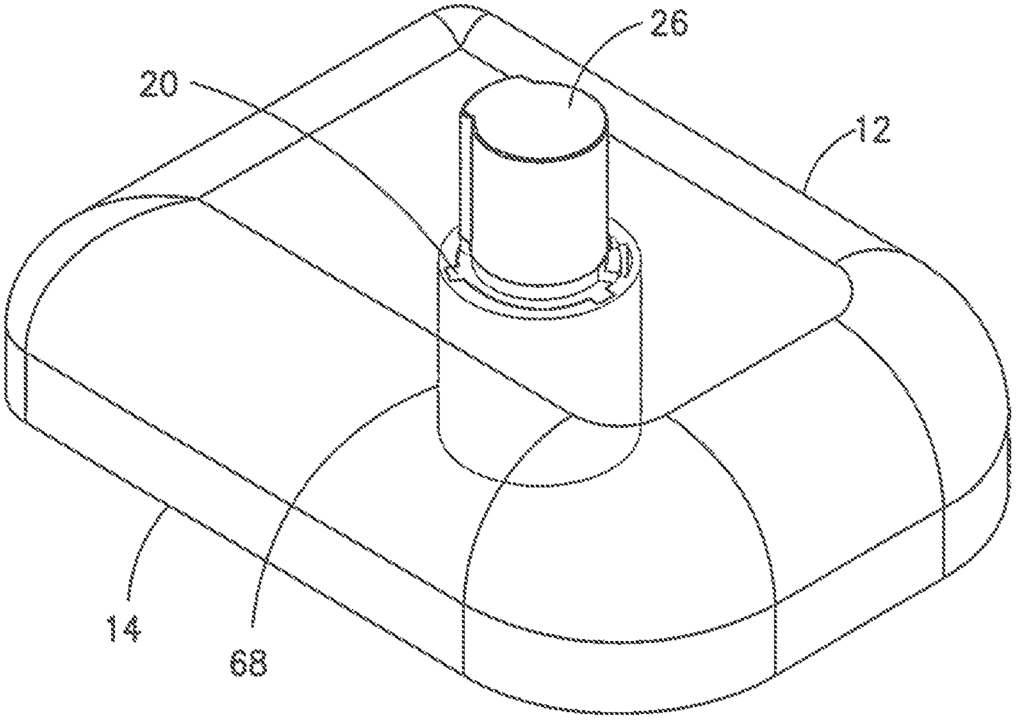
FIG. 7 is a perspective view of the actuator of the catheter insertion device in one embodiment of the invention.
Figure 9:
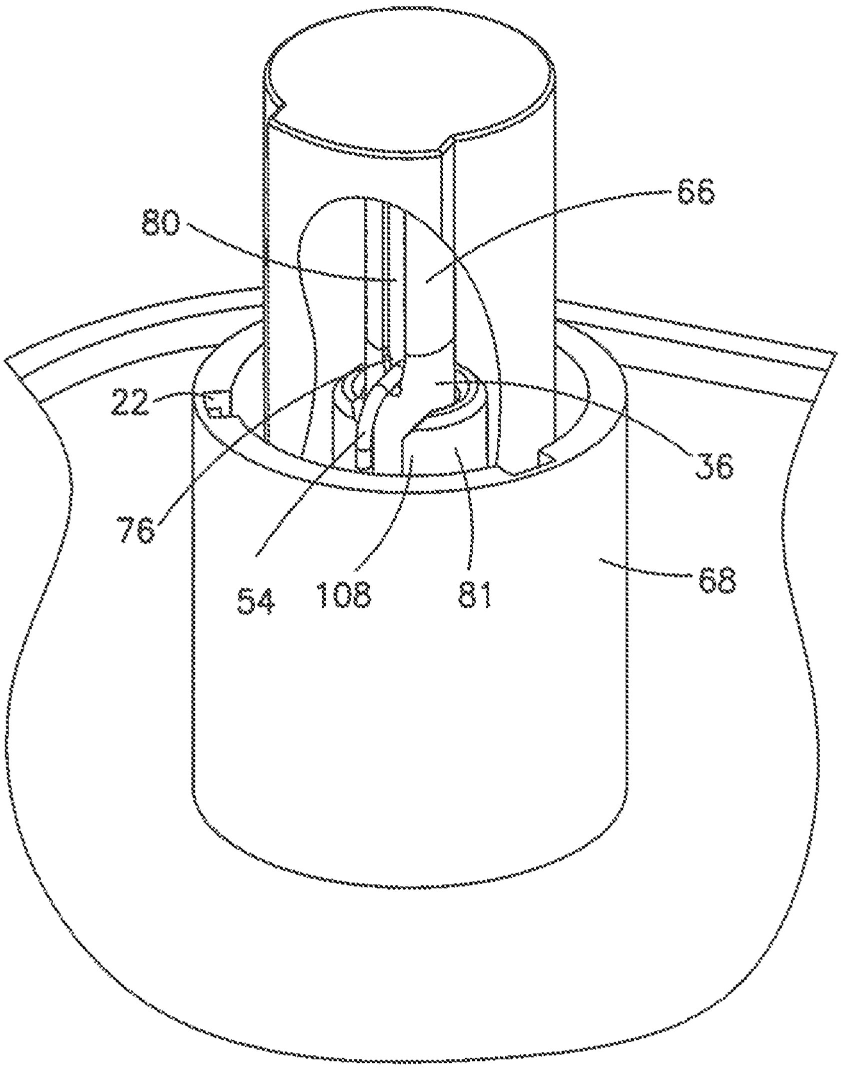
FIG. 9 is a partial perspective view showing the catheter insertion device with the insertion needle coupled to the needle carrier.

In the embodiment shown, actuator 26 has a cylindrical outer side wall 58 with a top wall 60 and a bottom distal end 62. Outwardly extending breakable or resilient tabs 20 are received in corresponding recesses 22 in housing to require a predetermined force to depress actuator 26 as shown in FIGS. 7 and 9. Cylindrical side wall 58 defines an interior annular cavity 64. In one embodiment of the invention, a substantially cylindrical shaped inner sleeve 66 extends from top wall 60 toward distal end 62 of the side wall 58 and is spaced inwardly from outer side wall 58. Sleeve 66 is concentric with side wall 58 and spaced inwardly to define annular cavity 64. In one embodiment, sleeve 66 has a length less than a length of side wall 64 so that the end of the sleeve 66 is spaced from bottom distal end 62 a distance complementing the dimension of catheter hub 36 so that the hub 36 is received within the actuator as shown in FIG. 8.

Figure 12:
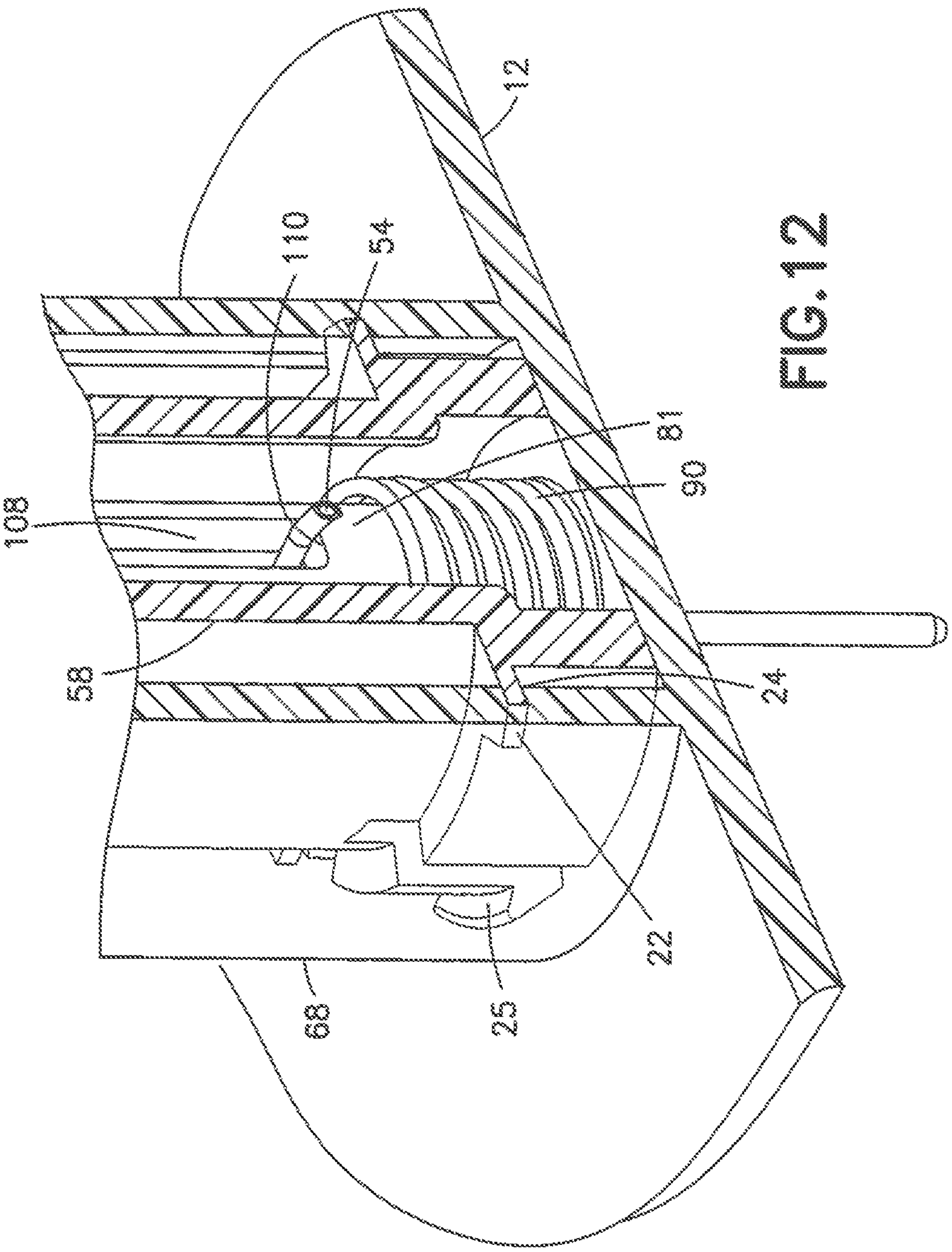
FIG. 12 is a partial cross-sectional view showing the connecting portion of the insertion needle engaging an inner wall of the housing to separate the needle from the needle retainer.
Figure 13:
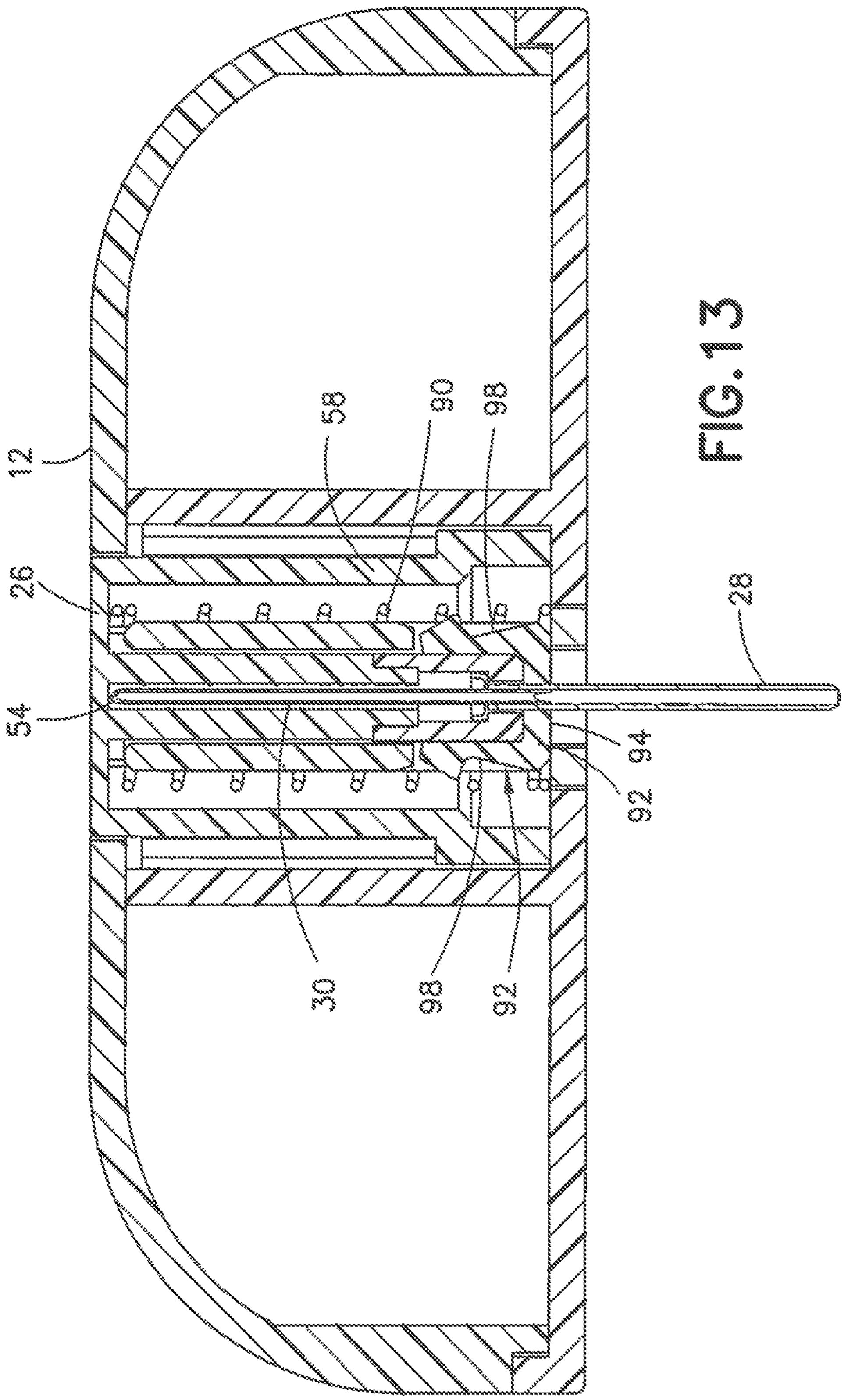
FIG. 13 is a cross-sectional view showing needle in the retracted position.

In the embodiment shown, a cylindrical wall 68 is provided within housing 12 for defining a cavity 70 or passage for receiving actuator 26 and allowing sliding movement of actuator 26 with respect to the housing 12 and base 14. In one embodiment, cylindrical wall 68 is integrally formed with base 12. Cylindrical side wall 68 is provided with a recess at a top end and a recess or rib 24 toward a bottom end at or near base 14 as shown in FIG. 12. The outwardly extending detent 20 can be provided to project outwardly from side wall 58 and has a dimension to be received in the respective recesses to retain the actuator in the deployed position. Other mechanisms can be used to retain or lock the actuator in a deployed position such as by a hook 25 that mates with a corresponding recess or tab on an inner surface of wall 68.

Insertion needle 30 is coupled to a needle carrier which is formed as part of catheter hub 36. In the embodiment shown, needle carrier has a cylindrical shape forming a sleeve that slides within cavity 74 of inner wall 81. The needle carrier is formed by a V-shaped notch 76 shown in FIG. 10 having a dimension to receive connecting portion 54 of needle 30 so that downward movement of catheter hub 36 carries insertion needle 30 to the second extended position. The connecting portion 54 can be received in the notch 76 by a friction fit. Connecting portion 54 of needle 30 in the embodiment shown extends substantially perpendicular to the main longitudinal portion of needle 30 and is connected to the fluid supply for introducing the fluid to the catheter during use. As shown in FIGS. 8 and 9, inner sleeve 66 of actuator 26 has a longitudinal slot 80 to enable connecting portion 54 of needle 30 to slide within actuator 26 in a linear direction along the longitudinal dimension of the slot 80.

Housing 12 is provided with an inner wall 81 concentric with wall 68 to form an axial passage 82 for catheter hub 36 and inner sleeve 66 of actuator as shown in FIG. 8. In one embodiment, inner wall 81 is connected to base 12 by a connecting portion 83. Inner wall 81 has a top end at the top face of housing 12 for receiving actuator and guiding actuator 26 while actuator 26 moves between the first position and the second position. As shown in FIGS. 8 and 10, inner wall 81 includes openings 84 at the bottom end adjacent base 14 formed by the connecting portions 83. In the embodiment shown, the distal end of inner sleeve 66 of actuator 26 is coupled to catheter hub 36 so that catheter hub 36 moves with actuator 26 to the extended position when the device is deployed.

Figure 11:
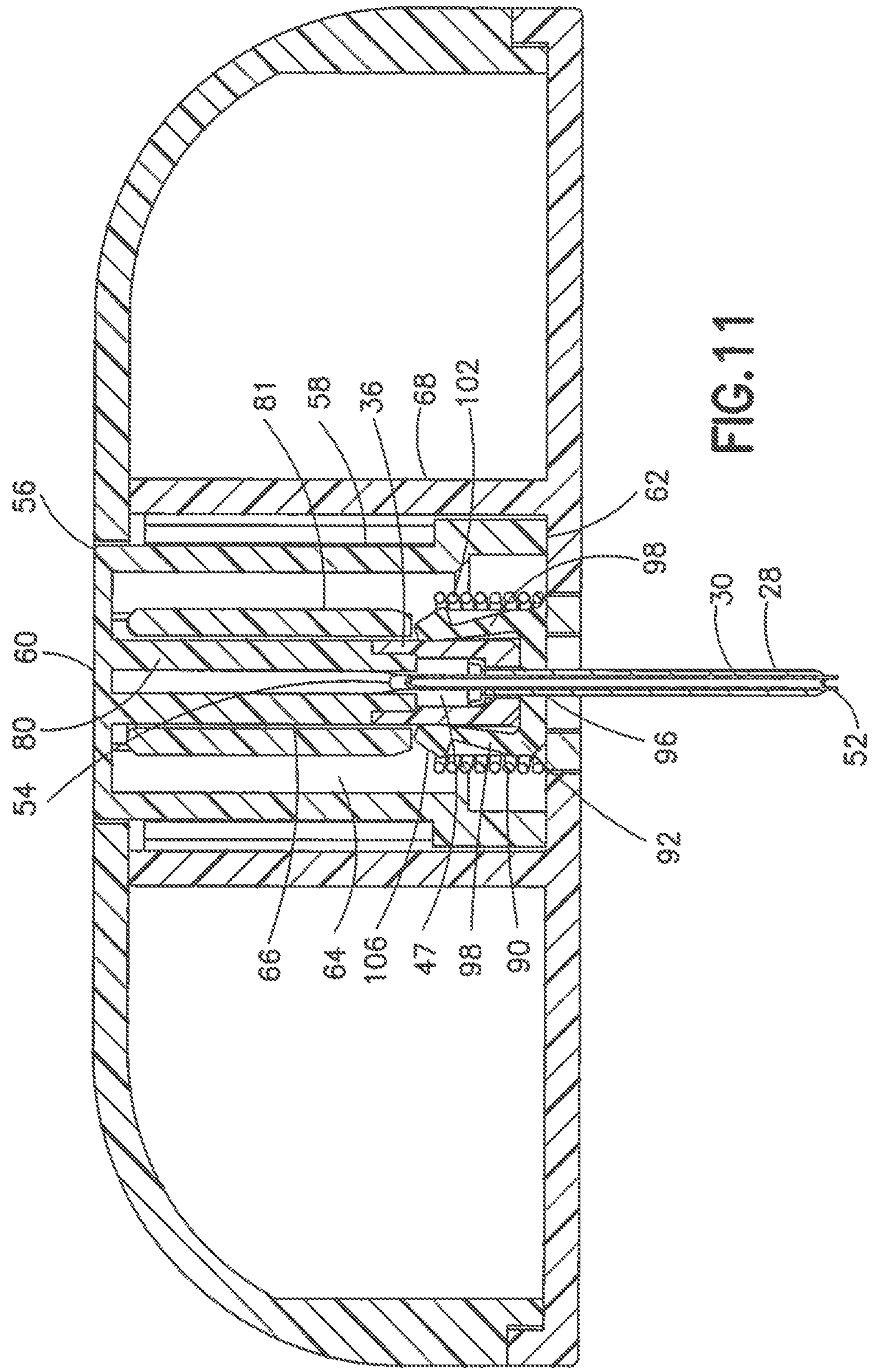
FIG. 11 is a cross-sectional view showing the catheter and needle in the deployed position and the catheter hub engaging the spring retainer to release the spring.

A biasing member is provided to bias insertion needle 30 upwardly with respect to the bottom wall. A spring 90 and a spring retainer 92 are provided within housing 12 and within the cavity 70 defined by inner wall 68. As shown in FIGS. 8, 10 and 11, spring 90 is a coil spring surrounding inner wall 81, the center axis of cavity 70 and the opening provided in base 12 for the catheter 28 and needle 30. Spring retainer 92 can be made from a flexible or deformable material having a bottom wall 94 with an aperture 96 to receive catheter 28 and needle 30. At least one and typically three flexible and bendable legs 98 extend upwardly from bottom wall 94. Each leg 98 is provided with an outwardly extending tab 100 having a bottom face 102, a top face 104 and an inner face 106. Bottom face 102 extends substantially parallel to base 12 in the rest position to capture spring 90 between tabs 100 and base 12, as shown in FIG. 8 and FIG. 10. Inner face 106 in the initial position contacts the outer edge of inner wall 81 to retain legs 98 in the outward position shown in FIG. 8. In the embodiment shown, spring 90 is initially in a compressed state so that spring 90 biases spring retainer 92 in an upward direction toward and into contact with the bottom end of inner wall 81 shown in FIG. 10. In the embodiment shown, legs 98 engage an outer surface of inner wall 81 to retain legs 98 flexed outward to the position shown in FIG. 8 to retain spring 90 in the compressed state. In the embodiment shown, the bottom edge of inner wall 81 has a slight taper complementing the slight outward taper of inner surfaces 106 of legs 98.

During use, the infusion set is positioned against the skin of the patient by an adhesive in the desired location. Initially, actuator 26 is in the position shown in FIG. 8 extending above the top face of housing 12 with catheter 28 and needle 30 retracted within housing 12. The device is deployed by the user pressing in a downward direction on actuator 26. The downward force on actuator 26 pushes catheter hub 36 with needle 30 removably coupled to catheter hub 36 to an extended position shown in FIG. 10 where the distal end of catheter hub 36 contacts bottom wall 94 of spring retainer 92 and needle 30 and the catheter penetrates the skin of the patient. At this point, further movement of actuator 26 pushes spring retainer 92 downward toward base 12 and away from inner wall 81 to the position shown in FIG. 11. As shown in FIG. 12, inner wall 81 has a longitudinal slot 108 to enable connecting portion 54 of needle 30 to slide along the length of inner wall 81. In FIG. 12, spring retainer 92 is not shown for clarity. Spring retainer 92 is normally positioned with spring 90 as shown in FIG. 8. A bottom edge 110 of slot 108 is spaced from the base 12 a distance so that connecting portion 54 contacts bottom edge 110 as actuator 26 is moved to the position shown in FIG. 11 to separate needle 30 from catheter hub 36. The downward movement of actuator 26 and catheter hub 36 to the position shown in FIG. 11 separates connecting portion 54 from notch 76 in needle carrier 36 as shown in FIG. 12 to allow connecting portion 54 and needle 30 to retract by the spring 90 within the inner wall 81 and the inner sleeve 66. In this position, inner face 106 of the tabs 100 are separated from the inner wall 81 so that tabs 100 deflect inwardly toward each other and the center axis of spring retainer 92 so the bottom face 102 of tabs 100 are separated from the end of spring 90, thereby allowing spring 90 to expand to the position shown in FIG. 13. Spring 90 engaging the bottom surface 102 biases legs 98 inwardly so that spring 90 slides over the tabs 100. The expansion of spring 90 enables the top end of spring 90 to engage connecting portion 54 of needle 30 and retract the needle 30 from catheter 28 into the cavity of inner sleeve 66. In preferred embodiments, needle 30 remains at least partially within catheter 38 for supplying a pharmaceutical agent through catheter 28 to the patient.

In another embodiment of the invention shown in FIGS. 14-17, the catheter insertion device is included in an infusion set 120 having a housing 122 and a base 124 in a manner similar to the previous embodiment. An actuator 126 is slidably received in an opening 128 in housing 122.

Figure 15:
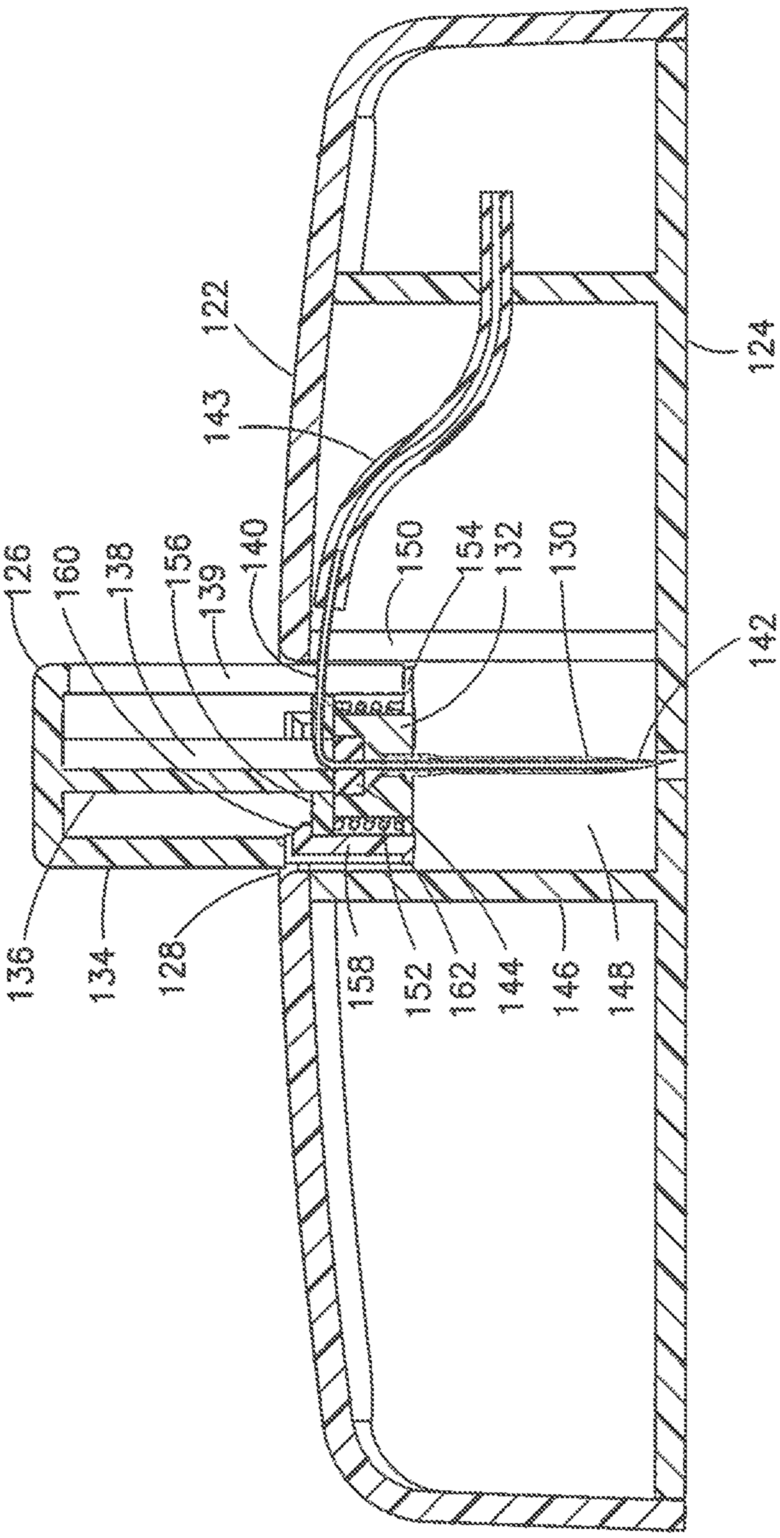
FIG. 15 is a cross-sectional view showing the actuator and spring assembly in the initial compressed state.
Figure 16:
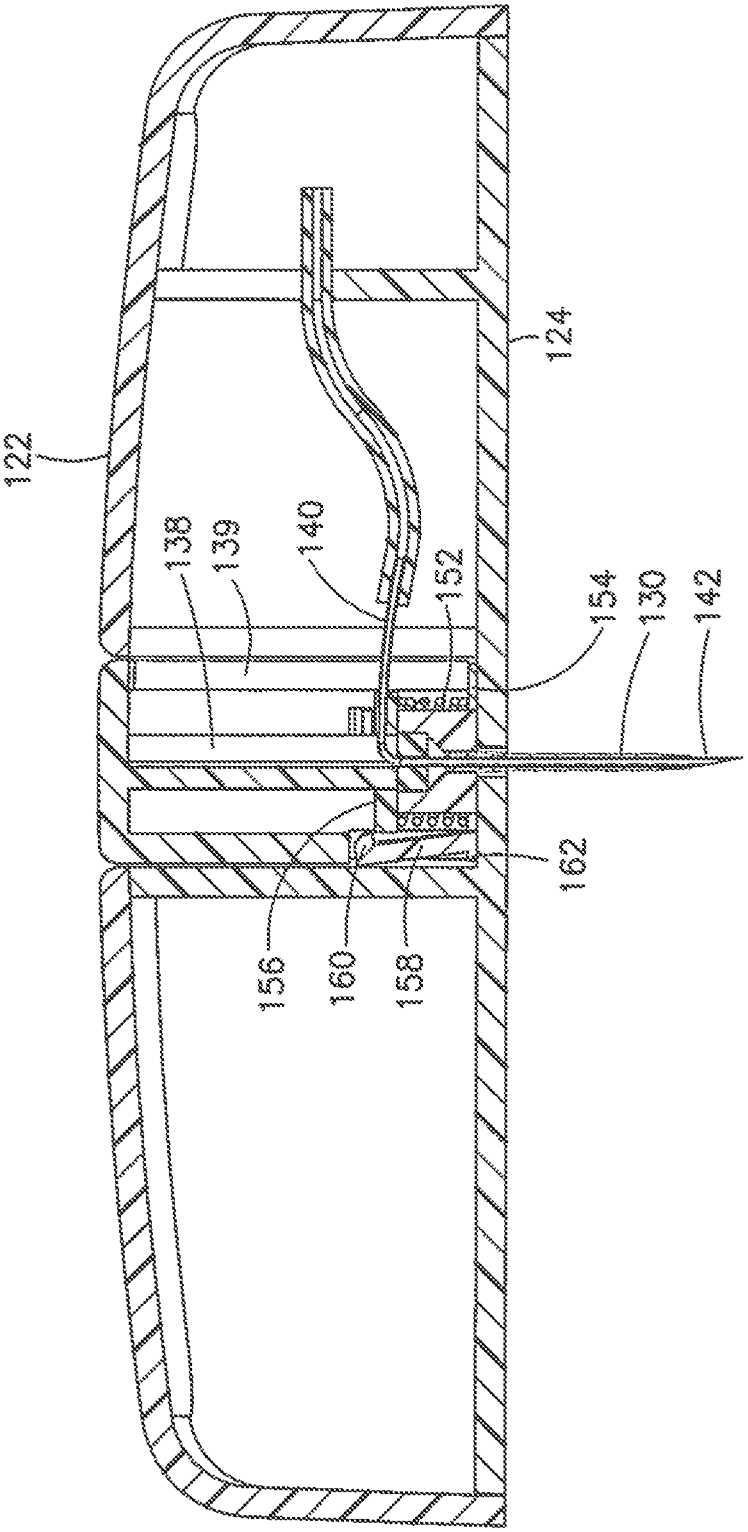
FIG. 16 is a cross-sectional view showing the actuator, catheter and needle in the deployed position.
Figure 17:
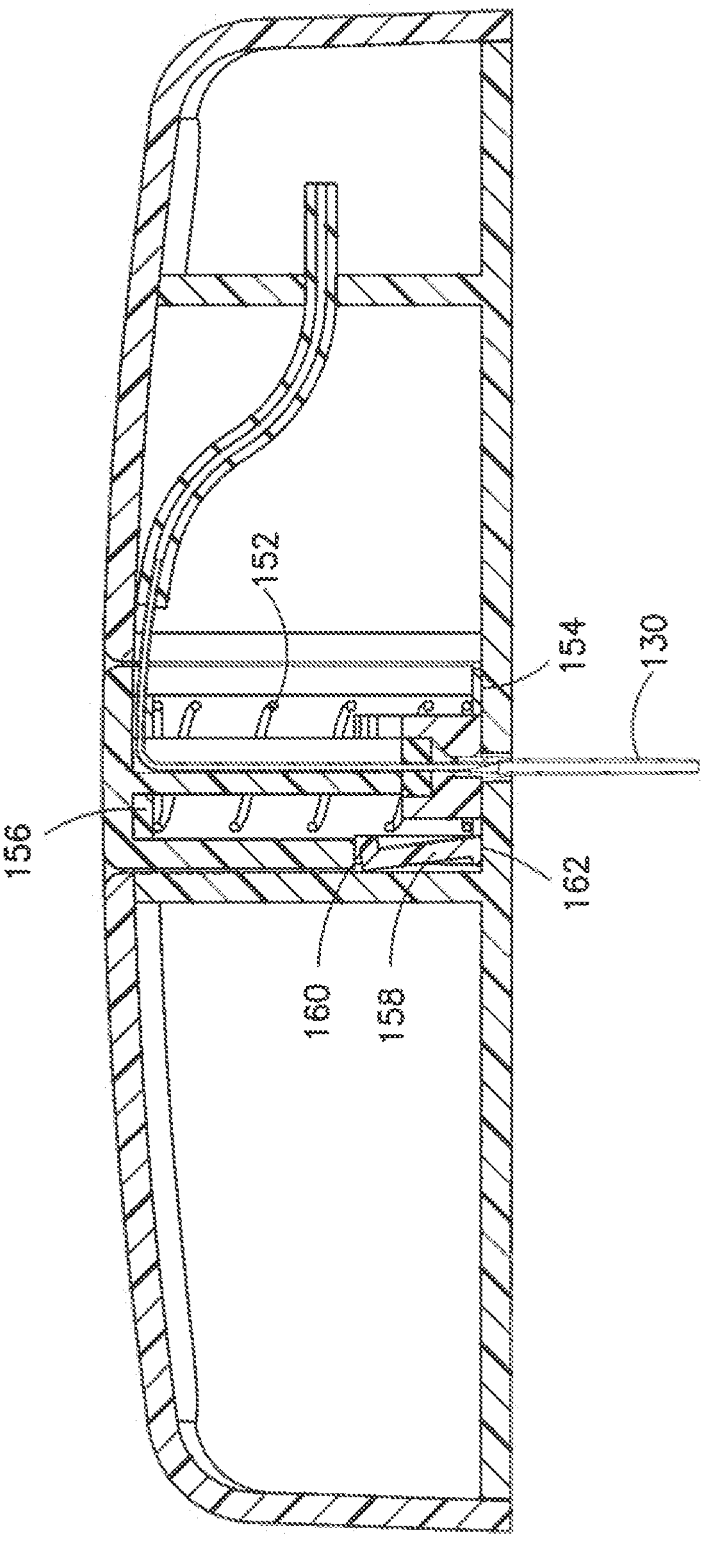
FIG. 17 is a cross-sectional view showing the spring being released to retract the needle from the catheter.

A catheter 130 is coupled to a catheter hub 132 which is coupled to actuator 126. Actuator 126 includes an outer wall 134 and an inner wall 136. Inner wall 136 includes a longitudinal slot 138 for slidably receiving a connecting portion 140 of the introducer needle 142. Outer wall 134 includes a longitudinal slot 139 aligned with slot 138 for receiving the connecting portion 140 as shown in FIGS. 15-17. Needle 142 extends through a septum 144 received within catheter hub 132. A funnel is received in catheter hub 132 and is connected to catheter 132 as in the previous embodiment. In one embodiment, catheter 130 is a flexible catheter suitable for introducing a substance to a patient. Housing 122 has an inner wall 146 defining a cavity 148 to receive actuator 126 in a sliding manner as in the previous embodiment. A slot 150 extends the longitudinal length of inner wall 146 to allow connecting portion 140 of needle 142 to slide between a retracted position shown in FIG. 15 and an extended position shown in FIG. 16. Needle 142 is connected to a flexible supply tube 143 that is connected to a reservoir and pump as in the previous embodiment.

Figure 14:
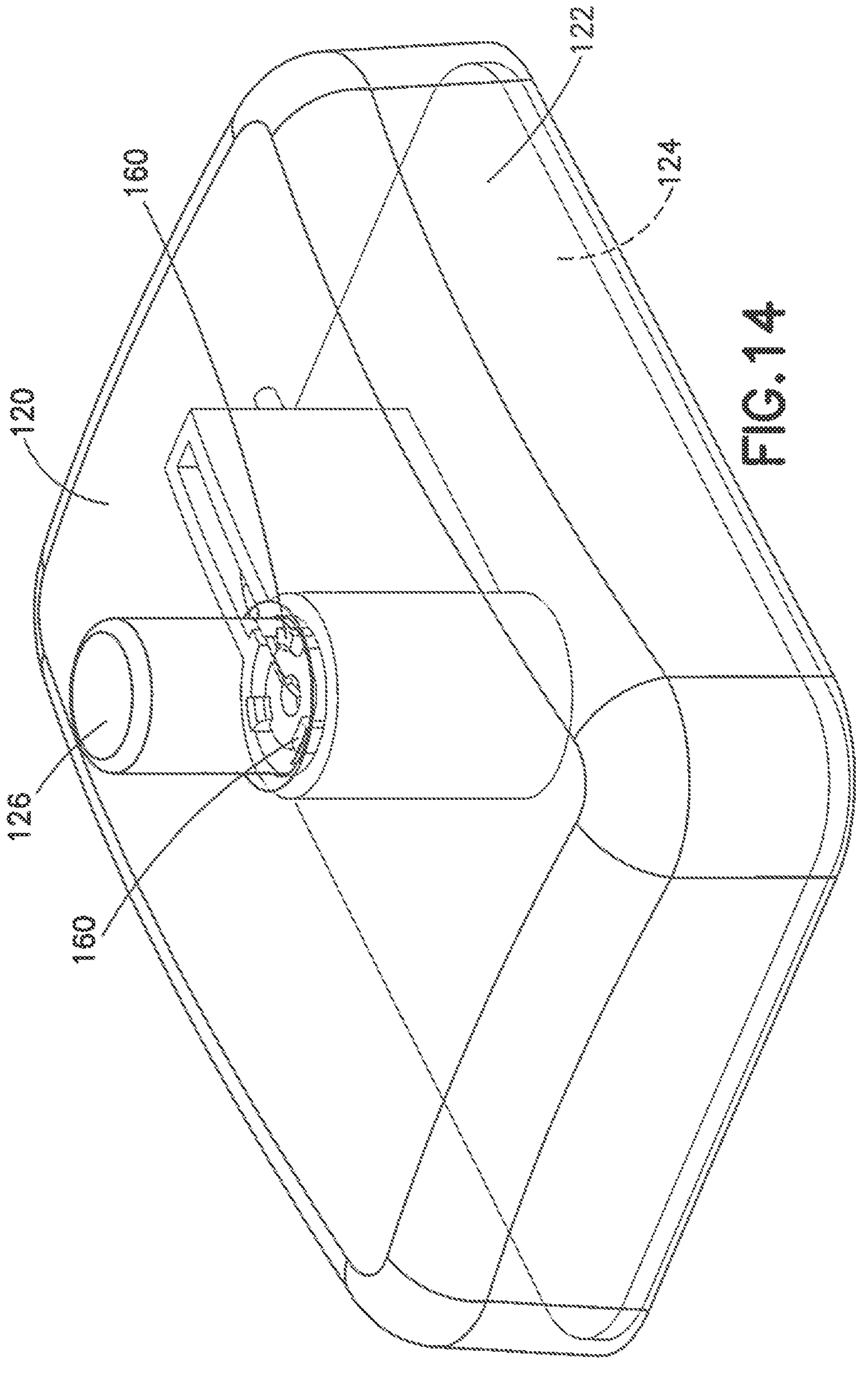
FIG. 14 is a perspective view in a second embodiment of the invention showing the spring assembly coupled to the actuator.

A biasing member is provided to bias needle 142 away from base 124 and to retract needle 142 with respect to catheter 130. A spring 152 and spring retainer 154 are coupled to actuator 126 to define a biasing member for retracting needle 142 from catheter 130. In the embodiment shown, spring 152 is a coil spring which is initially in a compressed state surrounding catheter hub 132. In this embodiment, spring retainer 154 is in the form of an outwardly extending flange extending radially outward from catheter hub 132 and forming a surface for contact with a bottom end of spring 152. Spring retainer 154 can be integrally formed with catheter hub 132. An annular shaped disc 156 slides on inner wall 136 within the annular cavity formed between outer wall 134 and 136. Disc 156 defines a surface for contacting a top end of spring 152. A top face of disc 156 includes a radially extending recess for receiving connecting portion 140 of needle 142. A movable latch 158 is coupled to spring retainer 154 as shown in FIG. 15. As shown in FIG. 14, three latches 158 are spaced equally around the perimeter of disc 156. Movable latch 158 has a top end with an inwardly extending hook 160 for hooking onto the top surface of disc 156 as shown in FIG. 15. A bottom end of latch 156 has an outwardly extending leg 162. In one embodiment, movable latch 158 is able to pivot around the distal end of leg 162 so that hook 160 is able to move radially outward to release and disengage disc 156.

During use, infusion set 120 is positioned on the skin of the patient in the desired location. Actuator 126 is manually depressed downward toward the skin of the patient to deploy catheter 130 and needle 142. The downward force pushes catheter hub 132 and disc 156 toward base 124 so that catheter 130 and insertion needle 140 to penetrate the skin of the patient as shown in FIG. 16. Actuator 126 is moved to the position shown in FIG. 16 where latch 156 contacts base 124 and pivots outwardly to unhook from disc 156 thereby releasing disc 156 and spring 152. Spring 152 then expands carrying disc 156 and needle 142 to the retracted position shown in FIG. 17.

In one embodiment, each latch 158 is coupled to or integrally formed with spring retainer 154 and spaced outwardly from catheter holder 132. The downwardly movement of catheter holder 132 causes the bottom end of latch 158 to contact bottom wall 124 in the extended deployed position. Contact of latch 158 with bottom wall 124 causes an outwardly pivoting movement of latch 158 away from spring retainer 156 to release spring retainer 156 and spring 152. The downward movement of actuator 126 and the force applied to disc 156 releases the tension between hook 160 of latch 158 and disc 156 to allow hook 160 to separate from disc 156. In one embodiment, latch 158 in a rest position extends at an outward angle from catheter hub 132 in the position shown in FIG. 16. The latches 158 in the loaded position shown in FIG. 15 are pushed inwardly so that hook 160 engages disc 156. Spring 152 biases disc 156 into contact with hook 160 so that hook 160 is retained in the latched position shown in FIG. 15. The downward force of catheter hub 132 and disc 156 can release tension on spring 152 to enable latch 158 to move away from catheter hub 132 to disengage hook 160 from disc 156.

While various embodiments have been shown and described, it will be understood by those skilled in the art that various changes and modifications can be made without departing from the scope of the invention as defined in the appended claims.

The invention claimed is:

1. A catheter insertion device comprising:
- a housing;
- a catheter having a catheter hub;
- an introducer needle within said catheter;
- a single spring disposed in said housing;
- a spring retainer retaining said spring in a compressed state between a surface of said housing and said spring retainer; and
- an actuator having an end engaging said catheter hub, said actuator being movable from a first position where said catheter and introducer needle are positioned within said housing, and an extended second position where said catheter and introducer needle extend from said housing, and where said catheter hub engages said spring retainer when said actuator is in said extended second position to release said spring to engage said introducer needle and retract said introducer needle into said actuator.

2. The catheter insertion device of claim 1, wherein said spring retainer has a first end engaging a base of said housing and a second end engaging a proximal end of said spring to retain said spring in the compressed state.

3. The device of claim 1, wherein said actuator has a recess for receiving said spring when said spring is released to an expanded position.

4. A catheter insertion device comprising:
- a housing;
- a catheter having a catheter hub;
- an introducer needle within said catheter;
- a spring disposed in said housing;
- a spring retainer retaining said spring in a compressed state between a surface of said housing and said spring retainer; and
- an actuator having an end engaging said catheter hub, said actuator being movable from a first position where said catheter and introducer needle are positioned within said housing, and an extended second position where said catheter and introducer needle extend from said housing, and where said catheter hub engages said spring retainer when said actuator is in said extended second position to release said spring to engage said introducer needle and retract said introducer needle into said actuator
- wherein said spring retainer has a first end engaging a base of said housing and a second end engaging a proximal end of said spring to retain said spring in the compressed state; and
- said spring retainer includes a plurality of flexible legs with an outwardly extending tab engaging said proximal end of said spring, and where said catheter hub engages said spring retainer to move said tabs and release said spring.

5. The catheter insertion device of claim 4, wherein said housing has an inner wall engaging said plurality of flexible legs of said spring retainer in a spring-engaging position when said actuator is in the first position, and where said spring retainer moves distally to separate said plurality of flexible legs from said from said inner wall when said actuator is in the extended second position.

6. A catheter insertion device comprising:
- a housing;
- a catheter having a catheter hub;
- an introducer needle within said catheter;
- a spring disposed in said housing;
- a spring retainer retaining said spring in a compressed state between a surface of said housing and said spring retainer; and
- an actuator having an end engaging said catheter hub, said actuator being movable from a first position where said catheter and introducer needle are positioned within said housing, and an extended second position where said catheter and introducer needle extend from said housing, and where said catheter hub engages said spring retainer when said actuator is in said extended second position to release said spring to engage said introducer needle and retract said introducer needle into said actuator;
- wherein said spring is configured to retract said introducer needle with respect to said catheter where a distal end of said introducer needle is positioned in a proximal end of said catheter, and where said introducer needle is connected to a fluid supply to supply fluid to said catheter for introducing the fluid into a patient.

7. The device of claim 6, wherein
- said catheter hub has a slot at a first end with a dimension to frictionally engage said introducer needle whereby said introducer needle is carried by said catheter hub during movement to said second position, and where said spring contacts said introducer needle to separate said introducer needle from said catheter hub to retract said introducer needle with respect to said catheter and catheter hub.

8. A catheter insertion device comprising:
a housing;
a catheter having a catheter hub;
an introducer needle within said catheter;
a spring disposed in said housing;
a spring retainer retaining said spring in a compressed state between a surface of said housing and said spring retainer; and
an actuator having an end engaging said catheter hub, said actuator being movable from a first position where said catheter and introducer needle are positioned within said housing, and an extended second position where said catheter and introducer needle extend from said housing, and where said catheter hub engages said spring retainer when said actuator is in said extended second position to release said spring to engage said introducer needle and retract said introducer needle into said actuator;
wherein said introducer needle has a main portion and a connecting portion connected to a fluid supply, said connecting portion extending radially outward from said main portion, and where said spring engages said connecting portion to retract said introducer needle, and where a distal end of said introducer needle is positioned in a proximal end of said catheter when said introducer needle is in the retraced position to supply the fluid to the catheter.

9. A catheter insertion device comprising:
a housing;
an actuator having an axially extending slot, said actuator being movable with respect to said housing;
a catheter and catheter hub coupled to said actuator;
an introducer needle in said catheter and received in said slot of said actuator, said introducer needle connected to a fluid supply to supply fluid to said catheter when said introducer needle is in said retracted position;
a spring; and
a spring retainer to retain said spring in a compressed state;
said actuator being movable from a first position where said catheter and introducer needle are positioned in said housing and a second position where said catheter and introducer needle extend from said housing, said actuator being configured to release said spring from said spring retainer when said actuator is moved to said second position to expand said spring, where said spring engages said introducer needle and retracts said introducer needle into said actuator and said slot when said actuator is moved to said second position.

10. The device of claim 9, wherein
said spring retainer is coupled to said catheter hub and separable from said catheter hub when said catheter hub is moved to the second position.

11. The device of claim 9, wherein
said spring retainer is slidable relative to said actuator and is movable from a spring-retaining position to a deployed position to retract said introducer needle.

12. The device of claim 9, wherein
said catheter hub has a bottom end with an outwardly extending flange and a movable latch with an inwardly extending tab engaging said spring retainer, wherein said spring is retained between said flange and said spring retainer in the compressed state.

13. The device of claim 12, wherein
said movable latch separates from said spring retainer when said catheter hub contacts a base of said housing to release said spring retainer and said spring to retract said introducer needle.

14. The device of claim 9, wherein said introducer needle has a main portion and a connecting portion connected to the fluid supply, said connecting portion extending radially outward from said main portion, and where said spring engages said connecting portion to retract said introducer needle.

15. The device of claim 14, wherein a distal end of said introducer needle is positioned in a proximal end of said catheter when said introducer needle is in the retracted position to supply the fluid to the catheter.

16. The device of claim 14, wherein said slot receives said connecting portion for sliding between said first position and said second position.

17. A catheter insertion device comprising:
a housing;
a catheter and catheter hub;
an introducer needle within said catheter, said introducer needle having a connecting portion connected to a fluid supply;
a spring disposed in said housing;
a spring retainer in said housing and retaining said spring in a compressed state between said housing and said spring retainer; and
an actuator movable with respect to said housing, said actuator engaging said catheter hub, said connecting portion of said introducer needle extending from said actuator and being slidably received in said actuator, said actuator being movable from a first position where said catheter and introducer needle are in said housing and a second position where said catheter and introducer needle extend from said housing and said spring retainer releases said spring to retract said introducer needle into said actuator.

18. The device of claim 17, wherein
said catheter hub is removably coupled to said actuator and has a first end contacting said actuator and a second distal end configured to contact said spring retainer when said actuator is moved to the second position.

19. The catheter insertion device of claim 18, wherein
said housing has an inner wall engaging said spring retainer in a spring retaining configuration when said actuator is in the first position, and where said spring retainer separates from said inner wall to release said spring when said actuator is in the second position.

20. The catheter insertion device of claim 19, wherein said catheter hub moves said spring retainer from a first position where said inner wall engages said spring retainer to a second position where said spring retainer separates from said inner wall.

* * * * *